United States Patent [19]

Nakano et al.

[11] Patent Number: 5,536,850
[45] Date of Patent: Jul. 16, 1996

[54] SUBSTANCE DC114-A1

[75] Inventors: Hirofumi Nakano; Noboru Fujii; Tamio Mizukami; Youichi Uosaki, all of Machida; Katsunori Kita, Shizuoka; Eiji Kobayashi, Tokyo, all of Japan

[73] Assignee: Kyowa Hakko Kogyo Co., Ltd., Tokyo, Japan

[21] Appl. No.: 392,886

[22] PCT Filed: Jun. 14, 1994

[86] PCT No.: PCT/JP94/00956

§ 371 Date: Mar. 1, 1995

§ 102(e) Date: Mar. 1, 1995

[87] PCT Pub. No.: WO95/01981

PCT Pub. Date: Jan. 19, 1995

[30] Foreign Application Priority Data

Jul. 9, 1993 [JP] Japan ................................. 5-170455

[51] Int. Cl.⁶ ..................... C07D 311/78; C07D 311/94
[52] U.S. Cl. .................. 549/382; 549/414; 549/415; 549/417; 549/418
[58] Field of Search .................... 549/382, 414, 549/415, 417, 418

[56] References Cited

FOREIGN PATENT DOCUMENTS 0429209  5/1991  European Pat. Off. .

OTHER PUBLICATIONS

Chemical Abstracts, vol. 118, No. 17 (Apr. 26, 1993), 161044n.

*Primary Examiner*—Ba Kim Trinh
*Attorney, Agent, or Firm*—Fitzpatrick, Cella, Harper & Scinto

[57] ABSTRACT

The present invention relates to a novel substance DC114-A1 represented by the following formula (I):

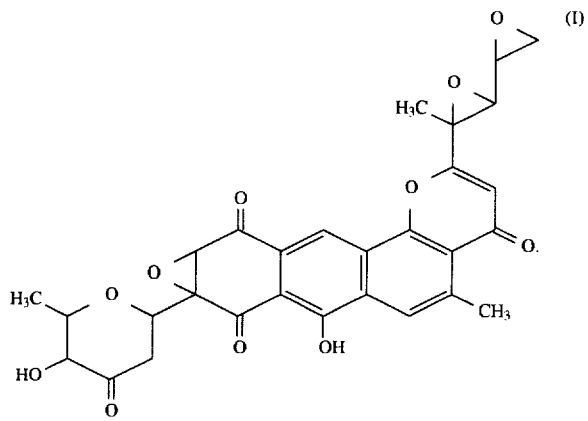

1 Claim, No Drawings

SUBSTANCE DC114-A1

This application is filed under 35 USC 371 of PCT/JP94/00956 dated Jun. 14, 1994.

TECHNICAL FIELD

The present invention relates to a novel substance DC114-A1 which has antibacterial and anti-tumor activity and is useful as antibacterial and anti-tumor agents.

BACKGROUND ART

Compound DC114-C which has a skeleton related to the present compound and which is represented by the following formula (II):

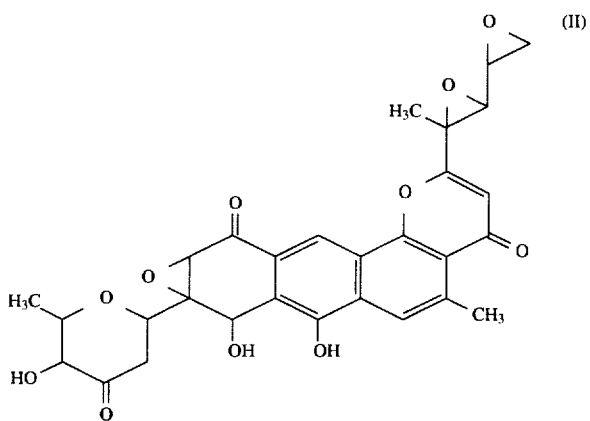

has been known (EP-A-0429209).

DISCLOSURE OF THE INVENTION

The present invention provides a novel substance DC114-A1 having antibacterial and anti-tumor activity which is represented by the following formula (I):

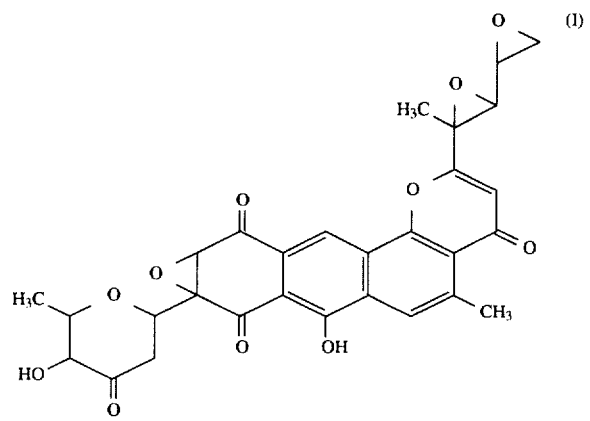

This compound can be produced by culturing a microorganism belonging to the genus Streptomyces.

The present invention is described in detail below.

The physicochemical properties of DC114-A1 are shown below.

(1) Molecular weight: 548

(2) Molecular formula: $C_{29}H_{24}O_{11}$ (3) Mass spectrum: High resolution FAB mass spectrum (matrix: m-nitrobenzyl alcohol): m/z amu
Found: 549.1402 $(M+H)^+$ Calculated for $C_{29}H_{25}O_{11}$: 549.1397

(4) Specific rotation: $[\alpha]_D^{26} = -53.8°$ (c=0.03, acetone)

(5) UV absorption spectrum (measured in methanol) $\lambda max(\epsilon)$; 224.5 (18,000), 275.0 (32,100), 408.0 (7,800)

(6) IR absorption spectrum (measured by the KBr method): $vmax\ cm^{-1}$; 3469, 1726, 1697, 1653, 1396, 1294, 1271, 1117, 1093.

(7) $^{13}C$-NMR spectrum (100 MHz, DMSO-$d_6$ solution): $\delta$ ppm (multiplicity); 206.0(s), 195.0(s), 189.2(s), 178.1(s), 164.3(s), 158.4(s), 154.2(s), 138.5(s), 128.2(s), 127.5(s), 125.0(s), 121.6(s), 120.8(d), 112.9(d), 110.8(d), 110.7(s), 75.3(d), 74.5(d), 64.2(d), 64.1(d), 63.9(s), 57.8(d), 57.1(s), 48.5(d), 43.7(t), 42.3(t), 22.9(q), 14.3(q), 12.5(q).

(8) $^1H$-NMR spectrum (400 MHz, DMSO-$d_6$ solution): $\delta$ ppm [integration, multiplicity, coupling constant (Hz) ]; 12.34(1H, br.s), 8.18(1H, s), 7.83(1H, s ), 6.46(1H, s), 5.47(1H, m), 4.85 (1H, dd, 11.4, 3.1), 4.51(1H, dq, 6.7, 6.7), 4.43(1H, br.d, 6.7), 4.31(1H, s), 3.26(1H, ddd, 6.6, 4.1, 2.5), 3.19(1H, d, 6.6), 2.95(1H, t, 4.7), 2.88(1H, dd, 5.0, 2.5), 2.85(1H, dd, 14.0, 11.4), 2.80(3H, d, 0.8), 2.57(1H, dd, 14.0, 3.1), 1.88(3H, s), 1.15(3H, d, 6.7) .

(9) Solubility: Soluble in dimethylsulfoxide (DMSO), methanol and acetone; sparingly soluble in water, ethyl acetate, chloroform and n-hexane.

(10) Color reaction: Positive to the iodine test

(11) Color and property of the substance: Yellow powder

(12) Thin layer chromatography: silica gel thin layer (HPTLC plate Art. 15647, produced by Merck & Co., Inc.)

The Rf value obtained by using toluene:acetone solution (2:1 v/v) as a developing solvent was 0.4.

The Rf value obtained by using chloroform:methanol (20:1 v/v) as a developing solvent was 0.6.

After the development, the spot of DC114-A1 can be detected by bioassay using *Bacillus subtilis*, by using hot sulfuric acid, or by ultraviolet absorption.

The biological activities of DC114-A1 are described below. The compound DC114-C described above was used for comparison.

(A) Antibacterial activity against various bacteria

The minimum inhibitory concentration (MIC) against the growth of various bacteria is shown in Table 1. The antibacterial activity was determined by the agar dilution method using a medium (pH 7) which comprises 3 g/l Bacto-tryptone (produced by Difco Laboratories), 3 g/l meat extract, 1 g/l yeast extract, 1 g/l glucose and 16 g/l agar.

TABLE 1

| Bacteria tested | MIC (µg/ml) | |
|---|---|---|
| | DC114-A1 | DC114-C |
| *Staphylococcus aureus* ATCC 6538P | 0.04 | 0.16 |
| *Enterococcus faecium* ATCC 10541 | 0.16 | 0.16 |
| *Bacillus subtilis* No. 10707 | 0.33 | 0.33 |
| *Klebsiella pneumoniae* ATCC 10031 | 5.21 | 5.21 |
| *Escherichia coli* ATCC 26 | 5.21 | 20.83 |
| *Pseudomonas aeruginosa* Bin H No. 1 | 5.21 | 41.67 |
| *Salmonella typhi* ATCC 9992 | 5.21 | 20.83 |
| *Proteus vulgaris* ATCC 6897 | 2.60 | 5.21 |
| *Shigella sonnei* ATCC 9290 | 5.21 | 20.83 |
| *Candida albicans* ATCC 10231 | 5.21 | >83.33 |

(B) Growth inhibition against HeLaS$_3$ cells

HeLaS$_3$ cells (ATCC HTB22) were suspended in a medium comprising 10% fetal calf serum, 2 mM glutamine and MEM medium (produced by Nissui Pharmaceutical Co., Ltd.) (hereinafter referred to as medium A) to a concentration of $3\times10^4$ cells/ml. The cell suspension was put into wells of a 96-well microtiter plate in an amount of 0.1 ml per well. The cells in the plate were cultured at 37° C. for 20 hours in a $CO_2$-incubator. Subsequently, the test compound appropriately diluted with medium A was added to the wells in an amount of 0.1 ml/well. The cells were further cultured at 37° C. for one hour in the $CO_2$-incubator, and then the culture supernatant was removed. To the residue was added a medium comprising medium A and 0.02% Neutral Red in an amount of 0.1 ml per well, followed by culturing at 37° C. for one hour in the $CO_2$-incubator, whereby the cells were stained. After removal of the culture supernatant, the residue was washed once with physiological saline. The pigment was extracted with 0.001 N hydrochloric acid/30% ethanol, and the absorbance at 550 nm was measured by using a microplate reader. The concentration of the test compound at which the growth of the cells is inhibited by 50% ($IC_{50}$) was calculated by comparing the absorbance of untreated cells with those of the cells treated with the test compound at known concentrations. The result is shown in Table 2.

TABLE 2

| Test compound | $IC_{50}$ (nM) |
|---|---|
| DC114-A1 | 12 |
| DC114-C | 21 |

The process for producing DC114-A1 is described below.

DC114-A1 can be obtained by culturing a microorganism belonging to the genus Streptomyces and having the ability to produce DC114-A1 in a medium, allowing DC114-A1 to accumulate in the culture, and recovering DC114-A1 from the culture.

As the DC114-A1-producing strains of the present invention, any strains which belong to the genus Streptomyces and have the ability to produce DC114-A1 can be used. In addition, any mutants of such strains which are obtained by various artificial mutation methods such as UV irradiation, X ray irradiation and treatment with mutagens or by spontaneous mutation may also be used in the present invention, insofar as they have the ability to produce DC114-A1. A typical example of a suitable strain is DO-114 strain (EP-A-0429209).

The strain has been deposited with the Fermentation Research Institute, Agency of Industrial Science and Technology with accession number FERM BP-2641 under the Budapest Treaty (date of original deposit: Nov. 8, 1989).

The culturing method for the DC114-A1-producing strains is as follows.

For the culturing of the DC114-A1-producing strains used in the present invention, conventional methods for culturing actinomycetes are generally employed.

As the medium, either a synthetic medium or a natural medium may be used insofar as it appropriately contains carbon sources, nitrogen sources and inorganic substances which can be assimilated by the strains employed and the growth- and production-promoting substances required.

As the carbon sources, glucose, starch, dextrin, mannose, fructose, sucrose, lactose, xylose, arabinose, mannitol, molasses, etc. can be used alone or in combination. In addition, hydrocarbons, alcohols, organic acids, etc. may also be used according to the assimilability of the microorganism employed.

As the nitrogen sources, ammonium chloride, ammonium nitrate, ammonium sulfate, sodium nitrate, urea, peptone, meat extract, yeast extract, dry yeast, corn steep liquor, soybean powder, casamino acid, etc. can be used alone or in combination.

If necessary, inorganic salts such as sodium chloride, potassium chloride, magnesium sulfate, calcium carbonate, potassium dihydrogen phosphate, ferrous sulfate, calcium chloride, manganese sulfate, zinc sulfate, copper sulfate, etc. may be added. In addition, trace ingredients that promote the growth of the strain employed and the production of DC114-A1 may also be added to the medium.

As the method of culturing, liquid culture, especially submerged stirring culture, is preferably employed. Culturing is carried out at 16° to 37° C. preferably 25° to 32° C., and at pH 4 to 10, preferably 6 to 8. In general, by culturing for 1 to 7 days, the desired compound DC114-A1 is produced and accumulated in the culture broth and the microbial cells. In order to adjust the pH of the medium, aqueous ammonia, ammonium carbonate solution, etc. are used. When the amount of the product in the culture reaches the maximum, the culturing is discontinued.

For the isolation and purification of the desired compound DC114-A1 from the culture, an ordinary method for isolating a microbial metabolite from the culture can be utilized. For example, the culture is separated into culture filtrate and microbial cells by filtration. The microbial cells are extracted with chloroform, acetone, or the like. Then, the extract is mixed with the culture filtrate, and the resulting mixture is passed through a column of polystyrene adsorbent such as Diaion HP20 (produced by Mitsubishi Kasei Corporation) to adsorb the active substance, followed by elution with ethyl acetate, acetone, or the like. The eluate is concentrated, and the concentrate is subjected to silica gel column chromatography, high performance liquid chromatography, and the like to obtain DC114-A1. During the culture and purification steps, DC114-A1 can be traced by bioassay using *Bacillus subtilis* No. 10707, or by thin layer chromatography using the UV absorbance of DC114-A1 as indication.

BEST MODE FOR CARRYING OUT THE INVENTION

Example 1

Streptomyces sp. DO-114 strain (FERM BP-2641) was used as the seed strain. The strain was inoculated into 300 ml of a seed medium having the following composition in a 2-l Erlenmeyer flask, and cultured with shaking (rotation: 200 rpm) at 30° C. for 48 hours.

Composition of the seed medium: 5 g/l Bacto-tryptone (produced by Difco Laboratories), 5 g/l yeast extract, 3 g/l meat extract, 10 g/l soluble starch, 10 g/l glucose and 5 g/l calcium carbonate (pH 7.2 before sterilization)

The resulting seed culture was transferred into 15 l of a fermentation medium having the following composition in a 30-l jar fermentor at the rate of 10% (by volume), and culturing was carried out at 28° C. with stirring and aeration (rotation: 200 rpm, aeration: 15 l/min.).

Composition of the fermentation medium: 25 g/l glycerol, 25 g/l glucose, 15 g/l dry yeast, 0.5 g/l $KH_2PO_4$, 0.5 g/l $MgSO_4 \cdot 7H_2O$, 5 g/l calcium carbonate (pH 7.0 before sterilization, adjusted with NaOH)

Culturing was carried out for 80 hours without controlling the pH of the medium.

After the completion of culturing, 15 l of n-propanol was added to the culture, followed by stirring. The removal of the cells and precipitates by filtration gave 28 l of a filtrate. The filtrate was concentrated, and the concentrate was diluted with water. The resulting mixture was passed through a column packed with 10 l of a polystyrene adsorption resin, Diaion HP20 to adsorb the active substance. After impurities were eluted with deionized water and 50% methanol, the active substance was eluted with ethyl acetate. The active fraction thus eluted was concentrated and water was added to the concentrate, followed by extraction with ethyl acetate. The extract was dehydrated over sodium sulfate, and concentrated. The residue was applied to a silica gel column (BW300, Fuji Davison Chemical Co., Ltd.) and developed with toluene:acetone solution (4:1 v/v). The active fraction thus eluted was concentrated, and the concentrate was applied to a silica gel column (Lichroprep Si60 Art. 9390; produced by Merck & Co., Inc.) and developed with toluene:acetone solution (4:1 v/v). The active fraction eluted was concentrated to give 10 mg of DC114-A1 as yellow powder.

Industrial Applicability

According to the present invention, the novel substance DC114-A1 which has antibacterial and anti-tumor activity can be provided.

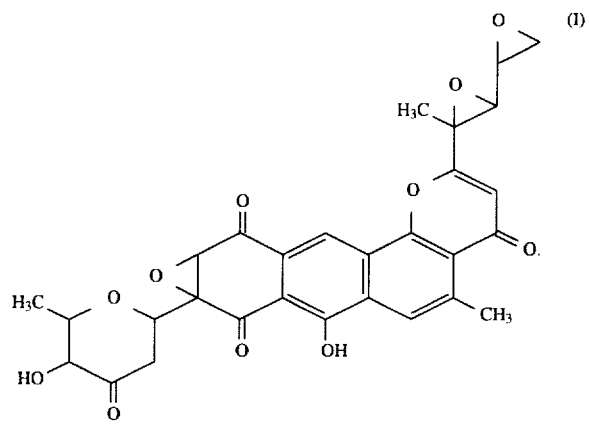

We claim:

1. Novel substance DC114-A1 which is represented by the following formula (I):